United States Patent [19]

Tsujimoto et al.

[11] Patent Number: 5,391,805
[45] Date of Patent: Feb. 21, 1995

[54] PROCESS FOR PRODUCING URETHANE COMPOUND

[75] Inventors: Tomoo Tsujimoto; Takashi Okawa, both of Nigata, Japan

[73] Assignee: Mitsubishi Gas Chemical Company Inc., Tokyo, Japan

[21] Appl. No.: 187,907

[22] Filed: Jan. 28, 1994

[30] Foreign Application Priority Data

Feb. 3, 1993 [JP] Japan .................... 5-016293

[51] Int. Cl.⁶ .................... C07C 269/00; C07C 269/04
[52] U.S. Cl. .................... 560/25; 560/24; 560/115; 560/157; 560/158
[58] Field of Search .................... 560/24, 25, 114, 115, 560/157, 158

[56] References Cited

U.S. PATENT DOCUMENTS

| | | | |
|---|---|---|---|
| 3,763,217 | 10/1973 | Brill | 260/471 C |
| 4,100,351 | 7/1978 | Romano et al. | 560/24 |
| 4,297,501 | 10/1981 | Becker et al. | 560/24 |
| 4,395,565 | 7/1983 | Romano et al. | 560/24 |
| 4,398,036 | 8/1983 | McCoy et al. | 560/24 |
| 5,171,830 | 12/1992 | Grey | 528/371 |

FOREIGN PATENT DOCUMENTS

| | | |
|---|---|---|
| 0436800A1 | 7/1991 | European Pat. Off. |
| 55-147253 | 11/1980 | Japan |
| 4-235954 | 8/1992 | Japan |

Primary Examiner—Jose G. Dees
Assistant Examiner—Barbara S. Frazier
Attorney, Agent, or Firm—Armstrong, Westerman, Hattori, McLeland & Naughton

[57] ABSTRACT

An urethane compound is produced in high yield under mild conditions by reacting a formamide compound with dimethyl carbonate in the presence of basic anion exchange resin as a catalyst or by reacting an amine compound with dimethyl carbonate in the presence of basic anion exchange resin as a catalyst and methyl formate. Separation and recovery of the catalyst and purification of the urethane compound can be carried out very readily, and since control of water content is not particularly required in this invention, an amine compound and dimethyl carbonate of poor quality can be used.

6 Claims, No Drawings

PROCESS FOR PRODUCING URETHANE COMPOUND

BACKGROUND OF THE INVENTION a) Field of the Invention

The present invention relates to a process for producing an urethane compound from a formamide compound or an amine compound and dimethyl carbonate as starting materials. An urethane compound is readily convertible to a corresponding isocyanate compound by thermal decomposition and thus can be used as an intermediate material for producing the isocyanate. Particularly an aliphatic diisocyanate compound derived from an aliphatic urethane compound having two carbamate ester groups in the molecule is useful as a raw material for producing polyurethane or polyurea having a distinguished resistance to yellowing.

b) Related Prior Art

An urethane compound can be produced from a nitro compound, an amine compound or a formamide compound as a main starting material. For example, a process using a nitro compound as a main starting material includes, for example, a process for carbonylation by reduction based on reaction of a nitro compound with carbon monoxide in the presence of an alcohol, as disclosed in JP-A-55-147253. A process using an amine compound as a main starting material includes a process for carbonylation by oxidation based on reaction of an amine compound with carbon monoxide and molecular oxygen or a nitro compound in the presence of an alcohol, as disclosed in U.S. Pat. No. 4,297,501. In these processes for carbonylation by reduction or that by oxidation, an expensive catalyst of platinum group metal such as Pd, Rh, etc. must be used, and reaction must be carried out at a high temperature under high pressure, resulting in an increase in the catalyst cost and capital investment. Thus, the processes suffer from these industrial disadvantages.

U.S. Pat. No. 4,398,036 discloses a process based on reaction of an amine compound with a carbamate ester or an amine compound with urea and alcohol. However, the process suffers from such disadvantages as a low reaction rate, that is, a low space-time yield, much formation of high boiling point by-products from the carbamate ester or urea, and the resulting difficulty in separation and recovery of the urethane compound.

Various processes based on reaction of an amine compound with dimethyl carbonate in the presence of a catalyst have been proposed as a process using an amine compound as a main starting material (U.S. Pat. No. 3,763,217; EP No. 48,371; U.S. Pat. No. 4,395,565). As a catalyst, a Lewis acid catalyst, a lead, titanium or zirconium-based catalyst, an alkali catalyst, etc. are used. However, these catalysts generally have a low reaction rate, and N-alkyl compounds are readily formed as by-products, resulting in a decrease in the yield of urethane compound. The processes suffer from these disadvantages. JP-A-64-85956 discloses a process based on a specific amine compound that hardly causes N-alkylation reaction as a side reaction, where the water content of dimethyl carbonate must be made to less than 0.2% and the amine compound and an alcoholate catalyst must be continuously or intermittently added to the reaction system.

The present inventors proposed a process based on reaction of a formamide compound with dimethyl carbonate in the presence of an alcoholate catalyst or reaction of an amine compound with dimethyl carbonate in the presence of an alcoholate catalyst and methyl formate (EP No. 0436800A1). The urethane compound obtained in the presence of an alcoholate catalyst of EP No. 0323514A1 and EP No. 0436800A1 can be converted to corresponding isocyanate by thermal decomposition.

However, in these processes, side reactions are considerably accelerated by the alkali catalyst in the urethane thermal decomposition step and thus it is indispensable to completely remove the catalyst. According to the conventional procedure, the alkali catalyst is neutralized by adding an acid to the reaction product solution, and the precipitated salt is separated from the solution. However, when the acid is excessively used or the neutralized salt has a high solubility, the salt itself gives an adverse effect on the thermal decomposition. Thus, extraction or washing with water is indispensable, and complicated purification procedures such as distillation, etc. are also indispensable. Use of the alkali catalyst has these disadvantages.

The present inventor also proposed an improvement of the process of EP No. 0436800A1, that is, a process based on reaction of a formamide compound with dimethyl carbonate, or reaction of an amine compound with dimethyl carbonate in the presence of methyl formate, at 100° to 200° C. without using any catalyst (JP-A-4-235954). The proposed process is distinguished in reaction in absence of catalyst, but it is inevitable to elevate the reaction temperature, and thus the resulting methyl formate is partly decomposed into methanol and carbon monoxide, and a high pressure reactor is required. Thus, the proposed process still has problems to be solved.

As described above, many processes have been as far proposed for the production of an urethane compound, but there have been still problems to be solved with respect to the urethane yield, separation and recovery of catalysts, treatment of by-products, purification of an urethane compound, higher capital investment, etc., and thus development of an industrially distinguished process for the production of an urethane compound has been keenly desired.

SUMMARY OF THE INVENTION

AS a result of extensive studies to solve the problems encountered in the production of an urethane compound as an intermediate product for producing isocyanates, the present inventor has found that an urethane compound can be produced in very high yield at a satisfactory reaction rate under mild conditions by reaction of a formamide compound with dimethyl carbonate or reaction of an amine compound with dimethyl carbonate in the presence of methyl formate, using a basic anion exchange resin as a catalyst, and further that separation, recovery and reuse of the catalyst and purification of the urethane compound can be readily carried out, and has established the present invention.

An object of the present invention is to provide a process for producing an urethane compound, which comprises reacting a formamide compound with dimethyl carbonate in the presence of a basic anion exchange resin.

Another object of the present invention is to provide a process for producing an urethane compound, which comprises reacting an amine compound with dimethyl carbonate in the presence of a basic anion exchange resin and methyl formate.

The reaction represented by the following equation (1) takes place in the present invention:

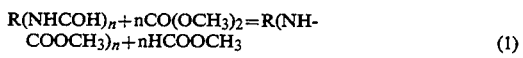

The formamide compound for use in the present invention is available from various sources, but it is preferable to prepare it by reaction of the corresponding amine compound with methyl formate, as given in the following equation (2):

wherein R represents aliphatic, alicyclic and aromatic hydrocarbon, and n is an integer of 1 to 3.

Methyl formate formed in the reaction (1) can be advantageously recovered and used as methyl formate for the reaction (2). The reaction (2) proceeds quantitatively at a high reaction rate merely by mixing an amine compound with methyl formate at the ordinary temperature under the atmospheric pressure without using any catalyst. The high reaction rate is characteristic of the reaction (2).

In other words, another preferable procedure for the reaction is to conduct the reactions (1) and (2) at the same time. That is, a corresponding urethane compound can be obtained by in-situ reaction of an amine compound with dimethyl-carbonate in the presence of methyl formate.

As will be shown in Comparative Examples which follow, an urethane compound can be formed by reaction of an amine compound with dimethyl carbonate in the absence of methyl formate, but the reaction rate is low and the urethane yield is low.

DETAILED DESCRIPTION OF THE INVENTION

The present invention will be described in detail below.

The formamide compound for use in the present invention as a main starting material can be classified into two groups: aromatic formamide compounds and aliphatic formamide compounds. Aromatic formamide compounds are compounds in which the formamide group(s) is bonded to an aromatic ring. Aliphatic formamide compounds are compounds in which the formamide group(s) is bonded to a saturated carbon. Thus, the aliphatic formamide compounds contain not only saturated aliphatic hydrocarbons bonded with formamide group(s), but also alicyclic hydrocarbons bonded with formamide group(s). Above all, aliphatic formamide compounds having two formamide groups in the molecule are preferably used in the present invention. Formamide compounds in such a molecular structure that aliphatic formamide groups are bonded to the saturated carbon and the skeleton has an aromatic ring are particularly preferable. Starting materials corresponding to industrially useful isocyanate compounds include, for example, N,N-[1,3-phenylene-bis-(methylene)]bis-formamide and its 1,4-isomer, N,N-[1,3-cyclohexyl-bis-(methylene)]bis-formamide and its 1,4-isomer, 3-formamidomethyl-3,5,5-trimethyl-1-formamidocyclohexane, 1,6-hexamethylene diformamide, etc.

The amine compound can also be classified into two groups: aromatic amine compounds and aliphatic amine compounds. Aromatic amine compounds are compounds in which the amino group(s) is bonded to an aromatic ring. Aliphatic amine compounds are compounds in which the amino group(s) is bonded to a saturated carbon. Thus, the aliphatic amine compounds contain not only saturated aliphatic hydrocarbons bonded with amino group(s), but also alicyclic hydrocarbons bonded with amino group(s). Aliphatic compounds are also preferable when an amine compound is used as a main material. Amine compounds in such a molecular structure that aliphatic amino groups are bonded to the saturated carbon and the skeleton has an aromatic ring are particularly preferable. Starting materials corresponding to industrially useful isocyanate compounds include, for example, m- and p-xylylenediamine, N,N-[1,3-cyclohexyl-bis-(methylene)]-bis-amine and its 1,4-isomers, isophorone-diamine, 1,6-hexamethylenediamine, etc.

Aliphatic urethane compounds as raw materials for aliphatic diisocyanate compounds having an added value can be obtained from these main starting materials. Likewise, when aromatic formamide compounds or aromatic amine compounds are used as starting materials in the present process, aromatic urethane compounds as intermediate products for producing aromatic diisocyanates having a wide range of applications can be obtained therefrom.

Dimethyl carbonate as an auxiliary raw material or methyl formate as an additive for use in the present invention may be commercially available products themselves or products further purified therefrom, when required. It is not necessary to strictly control water contents of these starting materials, auxiliary raw material and additive, because no metal alcoholate is used as a catalyst at all in the present invention. This is a distinguished advantage of the present invention.

In the present invention, 1 to 20 moles, preferably 1 to 10 moles, of dimethyl carbonate is used per mole of the formamido group of the formamide compound. Below one mole, there will remain unreacted formamide compound, whereas above 20 moles the space-time yield will be impractically lowered. When the amine compound is used as a main starting material in the process of the present invention, 1 to 20 moles, preferably 1 to 10 moles, of dimethyl carbonate is used per mole of the amino group. 0.01 to 5 moles, preferably 0.1 to 1 mole, of methyl formate is used per mole of the amino group. Below 0.01 mole no better reaction-accelerating effect by addition of methyl formate can be obtained, whereas above 5 moles the space-time yield will be unpreferably lowered.

The basic anion exchange resin for use in the present invention is basic anion exchange resins in such a structure that anion exchange groups are introduced to resin matrix of cross-linked structure. Strongly basic anion exchange resins are particularly preferable. The resin matrix for the basic anion exchange resins for use in the present invention includes, for example, styrenedivinylbenzene-based, cross-linked polystyrene, acrylic acid-based polyacrylate, ether group or carbonyl group-containing, heat-resistant aromatic polymers, etc.

It is known that anion exchange groups in ion exchange resins are generally amino groups, substituted amino groups, quaternary ammonium groups, etc. In case of the strongly basic anion exchange resins for use in the present invention, particularly preferable anion exchange groups are quaternary ammonium groups containing trialkyl-substituted nitrogen atoms (—N+R₃) or dialkylethanolamine anions, for example, —N+(CH₃)₂—(C₂H₄OH). Examples of the strongly basic anion exchange resins include Lewatit M500, Lewatit MP500 and Lewatit M504 (products of Bayer A. G., Germany); Diaion PA 306 (product of Mitsubishi Kasei Kogyo K. K., Japan); Amberlist A-26 (product of Rhom & Haas Co., USA); Dowex TG 550A (product of Dow Chemical Co., USA), etc.

In case of batch reaction, 1 to 90% by weight, preferably 10 to 50% by weight, of the strongly basic anion exchange resin is used on the basis of a concentration in the reaction solution. Below 1% by weight, no satisfactory reaction rate will be obtained, whereas above 90% by weight the catalyst cost will be higher, resulting in an economical disadvantage.

When the main starting material is in a solid state or the resulting urethane compound is precipitated in a solid state in the present invention, the reaction can be carried out satisfactorily when a solvent is added thereto. The solvent for this purpose must be inert is the raw material for the reaction and also to the resulting urethane compound. Examples of the solvent include alcohols such as methanol, ethanol, etc.; ethers such as tetrahydrafuran, dioxane, etc.; hydrocarbons such as benzene, toluene, etc.; and sulfolane, etc. The amount of the solvent for this purpose must be a necessary minimum, and usually is 1 to 10 parts by weight per one part by weight of the main starting material.

In the present invention, reaction temperature and reaction time depend on species of raw materials and the amount of catalyst to be used, and cannot be specifically defined. However, usually applicable reaction temperature is in a range of 20° to 100° C., particularly 50° to 70° C. Below 20° C. the reaction rate will be lower, whereas above 100° C. methyl formate will be decomposed or the catalyst will be deactivated. Usually applicable reaction time is 0.1 to 10 hours, particularly 0.5 to 5 hours.

In the present invention, reaction pressure must be higher than the vapor pressures of formamide compounds, amine compounds, dimethyl carbonate, methyl formate and urethane compounds, at the reaction temperature. It is also possible to conduct the reaction under a pressure exerted by an inert gas or under a pressure exerted by carbon monoxide to suppress the decomposition reaction of methyl formate. Generally, a preferable reaction pressure is in a range of atmospheric pressure to 10 atmospheres.

The present reaction can be carried out in any manner, so long as it can bring the raw materials and the strongly basic anion exchange resin as a catalyst into mutual contact. For example, the reaction can be carried out batchwise or continuously. Usually the reaction can be carried out continuously in a fluidized bed or a fixed bed. For example, the resulting methyl formate can be continuously withdrawn from the reaction system by reactive distillation.

Reaction product solution and catalyst can be separated from each other by simple operation in the present invention. Urethane compounds of good quality can be obtained by removing unreacted dimethyl carbonate, methyl formate and methanol from the reaction product solution by distillation.

PREFERRED EMBODIMENTS OF THE INVENTION

The present invention will be described in detail below, referring to Examples, which are not limitative of the present invention.

Example 1

5.4 g of N,N'-[1,3-phenylene-bis-(methylene)]-bis-formamide (which will be hereinafter referred to as "metaxylylene diformamide"), 16.5 g of dimethyl carbonate, and 10 ml of strongly basic anion exchange resin (Lewatit M504, product of Bayer AG, Germany), treated with an aqueous 2N NaOH solution in advance were charged wholely into a three-necked flask having a capacity of 100 ml, provided with a reflux condenser, a thermometer and a stirrer for agitation, and the flask was placed on a water bath. Reaction was carried out at an elevated reaction temperature of 60° C. for 3 hours under reflux. After the reaction, the reaction product solution was analyzed by the internal standard method of liquid chromatography, and it was found that methyl N,N'-[1,3-phenylene-bis-(methylene)]bis carbamate (which will be hereinafter referred to as "metaxylylene dicarbamate" was formed in yield of 98.9% on the basis of metaxylylene diformamide.

Example 2

Reaction was carried out in the same manner as in Example 1 except that the strongly basic anion exchange resin was replaced with Diaion PA306 (product of Mitsubishi Kasei Kogyo K. K., Japan). After the reaction, the reaction product solution was analyzed, and it was found that metaxylylene dicarbamate was formed in yield of 99.1% on the basis of metaxylylene diformamide.

Example 3

3.8 g of metaxylylene diamine, 16.2 g of dimethyl carbonate, 1.7 g of methyl formate and 10 ml of strongly basic anion exchange resin (Lewatit M504, product of Bayer A. G., Germany) were wholely charged into the same three-necked flask as used in Example 1 and the flask was placed on a water bath. Reaction was carried out at an elevated reaction temperature of 60° C. for 3 hours under reflux. After the reaction, the reaction product solution was analyzed, and it was found that metaxylylene dicarbamate was formed in yield of 98.1% on the basis of metaxylylenediamine.

Example 4

3.8 g of metaxylylenediamine, 16.2 g of dimethyl carbonate, 0.8 g of methyl formate and 10 ml of strongly basic anion exchange resin (Lewatit M500, product of Bayer A. G., Germany) were wholely charged into the same three-necked flask as used in Example 1, and the flask was placed on a water bath. Reaction was carried out at an elevated temperature of 60° C. for 3 hours under reflux. After the reaction, the reaction product solution was analyzed, and it was found that metaxylylene dicarbamate was formed in yield of 98.4% on the basis of metaxylylenediamine.

Example 5

4.0 g of N,N-[1,3-cyclohexyl-bis-(methylene)]bisamine, 16.5 g of dimethyl carbonate, 1.7 g of methyl formate and 10 ml of strongly basic anion exchange resin (Lewatit M504, product of Bayer A. G., Germany) were wholly charged into the same three-necked flask as used in Example 1, and the flask was placed on a water bath. Reaction was carried out at an elevated temperature of 60° C. for 3 hours under reflux. After the reaction, the reaction product solution was analyzed by the internal standard method of gas chromatography, and it was found that methyl N,N-[1,3-cyclohexyl-bis-(methylene)]bis-carbamate was formed in yield of 98.1% on the basis of N,N-[1,3-cyclohexyl-bis-(methylene)]bis-amine.

Example 6

3.5 g of 1,6-hexamethylenediamine, 17.6 g of dimethyl carbonate, 1.8 g of methyl formate and 10 ml of strongly basic anion exchange resin (Lewatit M504, product of Bayer A. G., Germany) were wholly charged into the same three-necked flask as used in Example 1, and the flask was placed on a water bath. Reaction was carried out at an elevated temperature of 60° C. for 3 hours under reflux. After the reaction, the reaction product solution was analyzed by the internal standard method of gas chromatography, and it was found that methyl 1,6-hexamethylene dicarbamate was formed in yield of 98.6% on the basis of 1,6-hexamethylenediamine.

Example 7

60 ml of strongly basic anion exchange resin (Lewatit M504, product of Bayer A. G., Germany) was filled in a stainless steel reactor tube (15 mm in inner diameter and 770 mm in length), and the tube was flushed with a nitrogen gas. Then, the catalyst bed temperature in the tube was kept at 60° C. under a pressure of 3 kg/cm$^2$ by passing hot water through the jacket around the tube.

Then, 3.5 g/hr of metaxylylenediamine and 16 g/hr of a liquid mixture of dimethyl carbonate and methyl formate (which was in a molar ratio of dimethyl carbonate/metaxylylenediamine=6.5 and a molar ratio of methyl formate/metaxylylenediamine=1.0) were supplied to the catalyst bed. After the composition of the reaction product solution reached the steady state, the reaction product solution was sampled and analyzed by liquid chromatography. It was found that metaxylylene dicarbamate was formed in yield of 98.2% on the basis of metaxylylenediamine.

Comparative Example 1

3.8 g of metaxylylenediamine, 16.2 g of dimethyl carbonate, and 10 ml of strongly basic anion exchange resin (Lewatit M504, product of Bayer A. G., Germany) were wholly charged into the same three-necked flask as used in Example 1, and the flask was placed on a water bath. Reaction was carried out at an elevated temperature of 60° C. for 3 hours under reflux. After the reaction, the reaction product solution was analyzed, and it was found that metaxylylene dicarbamate was formed in yield of 47.9% on the basis of metaxylylenediamine.

Comparative Example 2

3.8 g of metaxylylenediamine, 16.2 g of dimethyl carbonate and 15 ml of strongly basic anion exchange resin (Lewatit M504, product of Bayer A. G., Germany) were wholly charged into the same three-necked flask as used in Example 1, and the flask was placed on a water bath. Reaction was carried out at an elevated temperature of 70° C. for 7 hours under reflux. After the reaction, the reaction product solution was analyzed, and it was found that metaxylylene dicarbamate was formed in yield of 89.5% on the basis of metaxylylenediamine.

Comparison of comparative examples 1 and 2 with Example 1 reveals that when an amine compound is reacted with dimethyl carbonate in the absence of methyl formate, the reaction rate is low and the urethane yield is also low.

According to the present invention an urethane compound can be produced in high yield under mild conditions from a formamide compound or an amine compound and dimethyl carbonate by using a basic anion exchange resin as a catalyst, and furthermore separation and recovery of the catalyst and purification of urethane can be more readily carried out.

When a metal alcoholate catalyst of the prior art is used, it is necessary to remove water from the raw materials because water lowers the activity of the catalyst. On the other hand, because the auxiliary raw material, i.e., dimethyl carbonate forms an azetropic mixture with water, it is impossible to use low quality of dimethyl carbonate in the reaction. However, when a basic anion exchange resin is used, as in the present invention, it is not particularly necessary to control the water content and thus an amine compound and dimethyl carbonate of poor quality can be used. Thus, the present invention provides an industrially much distinguished process.

What is claimed is:

1. A process for producing an urethane compound, which comprises reacting a formamide compound with dimethyl carbonate in the presence of a basic anion exchange resin.

2. A process according to claim 1, wherein the formamide compound is an aliphatic formamide compound.

3. A process according to claim 1, wherein the basic anion exchange resin is a strongly basic anion exchange resin containing quaternary ammonium groups having a trialkyl-substituted nitrogen atom or quaternary ammonium groups having a dialkylethanolamine anion as ion exchange groups.

4. A process for producing an urethane compound, which comprises reacting an amine compound with dimethyl carbonate in the presence of a basic anion exchange resin and methyl formate.

5. A process according to claim 4, wherein the amine compound is an aliphatic amine compound.

6. A process according to claim 4, wherein the basic anion exchange resin is a strongly basic anion exchange resin containing quaternary ammonium groups having a trialkyl-substituted nitrogen atom or quaternary ammonium groups having a dialkylethanolamine anion as ion exchange groups.

* * * * *